United States Patent
Balinski et al.

(10) Patent No.: US 10,226,632 B2
(45) Date of Patent: Mar. 12, 2019

(54) METHODS AND SYSTEMS FOR CONTROLLING IMPLANTABLE MEDICAL DEVICES USING WEARABLE TECHNOLOGY

(71) Applicant: INTERNATIONAL BUSINESS MACHINES CORPORATION, Armonk, NY (US)

(72) Inventors: Peter A. Balinski, Elmhurst, NY (US); Sandeep Bazar, Warangal (IN); Pamela A. Nesbitt, Ridgefield, CT (US); John T. Olson, Tucson, AZ (US); Sandeep R. Patil, Pune (IN); Sachin C. Punadikar, Pune (IN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/438,144

(22) Filed: Feb. 21, 2017

(65) Prior Publication Data
US 2018/0236242 A1     Aug. 23, 2018

(51) Int. Cl.
*A61N 1/36* (2006.01)
*A61N 1/365* (2006.01)
*A61N 1/37* (2006.01)
*A61N 1/372* (2006.01)

(52) U.S. Cl.
CPC ....... *A61N 1/36585* (2013.01); *A61N 1/3718* (2013.01); *A61N 1/37252* (2013.01)

(58) Field of Classification Search
None
See application file for complete search history.

(56) References Cited

U.S. PATENT DOCUMENTS

| | | | | |
|---|---|---|---|---|
| 7,020,508 | B2 * | 3/2006 | Stivoric | A61B 5/0205 600/390 |
| 7,043,305 | B2 * | 5/2006 | KenKnight | A61N 1/36514 607/32 |
| 8,183,998 | B2 * | 5/2012 | Rao | A61B 5/0031 340/539.12 |
| 8,265,556 | B2 * | 9/2012 | Tekin | A61B 5/0022 455/41.1 |
| 8,401,661 | B2 * | 3/2013 | Vamos | A61N 1/37264 607/60 |
| 8,641,612 | B2 * | 2/2014 | Teller | A61B 5/01 600/300 |
| 8,653,966 | B2 | 2/2014 | Rao et al. | |
| 8,736,441 | B2 | 5/2014 | Rao et al. | |

(Continued)

OTHER PUBLICATIONS

IBM, "Wearable Device to Detect Potential Interference or Unauthorized Access Attempts to Implanted Medical Devices," An IP.com Prior Art Database Technical Disclosure, IP.com No. IPCOM000178330D, Jan. 22, 2009 (3 pages).

(Continued)

*Primary Examiner* — Brian T Gedeon
(74) *Attorney, Agent, or Firm* — Griffiths & Seaton PLLC

(57) ABSTRACT

Embodiments for controlling an implantable cardiac device by one or more processors are described. Data from at least one wearable device sensor is received. The implantable cardiac device is controlled based on the data.

18 Claims, 10 Drawing Sheets

(56) References Cited

U.S. PATENT DOCUMENTS

| | | | |
|---|---|---|---|
| 8,886,316 B1* | 11/2014 | Juels | A61N 1/37252 |
| | | | 607/31 |
| 9,149,189 B2 | 10/2015 | Proud | |
| 9,186,077 B2 | 11/2015 | Ma | |
| 2010/0094147 A1 | 4/2010 | Inan et al. | |
| 2014/0206977 A1 | 7/2014 | Bahney et al. | |
| 2014/0330336 A1* | 11/2014 | Errico | A61N 1/36021 |
| | | | 607/45 |
| 2015/0087933 A1 | 3/2015 | Gibson et al. | |
| 2015/0242812 A1 | 8/2015 | Nelson et al. | |
| 2016/0250490 A1* | 9/2016 | Hoffman | A61N 1/37252 |
| | | | 607/60 |
| 2016/0349790 A1* | 12/2016 | Connor | G06F 1/1694 |

OTHER PUBLICATIONS

IBM, "Smarter Sensor Based Portable Record Players for Therapies Impacting Health Care Systems," An IP.com Prior Art Database Technical Disclosure, IP.com No. IPCOM000192632D, Jan. 26, 2010 (3 pages).

Anonymous, "Wearable medical device, such as a defibrillator and/or one including physiological sensors, responding to mechanical tapping as means of interface/communication," An IP.com Prior Art Database Technical Disclosure, IP.com No. IPCOM000223162D, Nov. 6, 2012 (6 pages.).

* cited by examiner

METHODS AND SYSTEMS FOR CONTROLLING IMPLANTABLE MEDICAL DEVICES USING WEARABLE TECHNOLOGY

BACKGROUND OF THE INVENTION

Field of the Invention

The present invention relates in general to computing systems, and more particularly, to various embodiments for controlling implantable medical devices using wearable technology.

Description of the Related Art

Regular heartbeat is maintained by electrical signals in the heart. Due to various conditions, such as bradycardia and heart block, doctors often advise patients to use pacemakers to maintain these electrical signals. Pacemakers regulate heartbeat using electrical impulses that are delivered by electrodes, which cause the appropriate heart muscles to contract. A typical pacemaker includes, for example, a computerized generator, a battery, and wires with sensors (or electrodes) on one end. The electrical activity of the heart is detected by these electrodes, and data is sent to the computer in the generator through the wires. When an abnormality in the heart's rhythm is detected, the generator is directed by the computer to send electrical pulses to the heart through the wires. Rate responsive pacemakers read various internal parameters, such as blood temperature, breathing speed, pH value of body, etc., and to determine the functionality (e.g., type and/or rate of pace) that is implemented.

Some modern pacemakers are able to consider internal body factors (e.g., breathing speed, blood temperature, pH value, etc.) and take decision accordingly. However, in general, there are various external factors which may affect the functioning of the human body and its internal organs.

SUMMARY OF THE INVENTION

Various embodiments for controlling an implantable medical device, such as implantable cardiac device, by one or more processors are described. In one embodiment, by way of example only, a method for monitoring an implantable cardiac device, again by one or more processors, is provided. Data from at least one wearable device sensor is received. The implantable cardiac device is controlled based on the data.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE DRAWINGS

Figure 1:
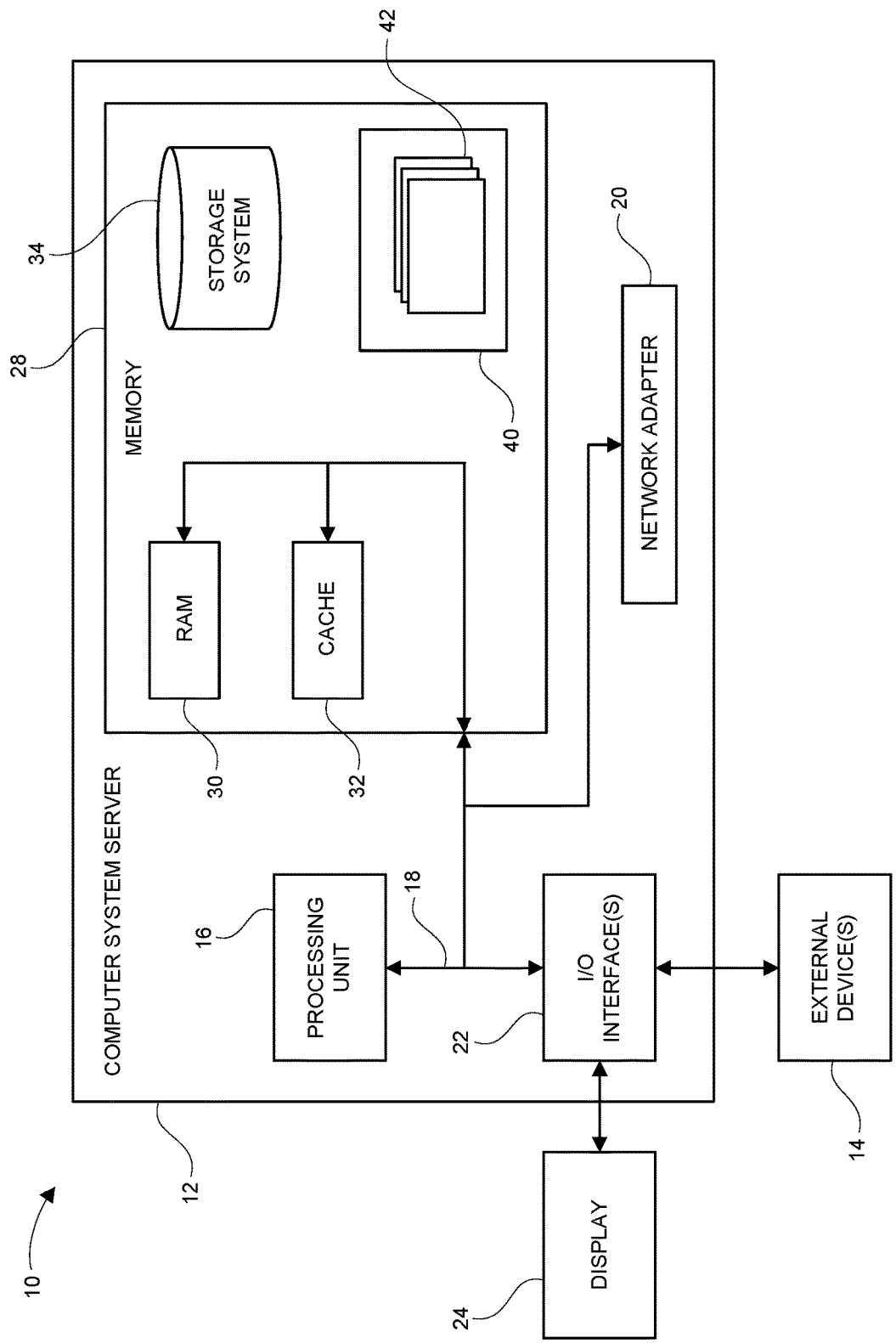
FIG. 1 is a block diagram depicting an exemplary computing node according to an embodiment of the present invention.

As previously indicated, regular heartbeat is maintained via electrical signals in the heart. In individuals who suffer from various conditions, such as bradycardia and heart block, a pacemaker may help maintain these electrical signals. Some modern pacemakers are configured to take into consideration internal body factors (e.g., breathing speed, blood temperature, pH value, etc.) and accordingly adjust the type and/or rate of pacing performed. However, various external factors may affect the functioning of the human body and its internal organs. With respect to a heart that is dependent on a pacemaker for proper functioning, it may be worthwhile to consider these external factors in determining the optimum type and/or rate of pacing. However, there are currently no mechanisms available in pacemakers that allow the pacemaker to know the user's state which may have an effect on which type/rate of pacing is appropriate for the patient at that time.

For example, pacemakers are typically programmed to regulate the heart rate between, for example, 50 and 100 beats per minute (bpm) without considering the physiological state of the patient, while in various states (or activity levels), such as sleeping or exercising, the functionality of heart changes. Some recent studies have suggested that it may be harmful for some otherwise healthy patients to have a heart rate maintained at greater than about 76 bpm while resting. Therefore, a conventional pacemaker that does not account for the physiological state of the patient may in fact be pacing the heart at a rate that is not ideal (e.g., with respect to the patient's health and/or conservation of battery power).

As another example, a relatively high breathing rate does not necessarily mean that the patient is in a state of increased activity (e.g., exercising). Rather, the high breathing rate may simply be the result of the patient being at a relatively high altitude with lower than typical oxygen levels. In such a situation, it may be undesirable for the pacemaker to increase the rate of pacing simply to match the patient's breathing rate.

Another factor which may affect pacemaker functionality is the presence of certain phenomena, such as magnetic fields. If the patient (and/or the pacemaker) remains in a magnetic field long enough, the functionality of the pacemaker may be affected. Additionally, some medication procedures (e.g., magnetic resonance imaging (MM) scans) may disrupt the operation of pacemakers.

Further, in some circumstances in which the pacemaker(s) needs to be serviced (e.g., a software upgrade), the patient must often visit a medical facility, and the process may require the device to be removed from the patient and replaced (perhaps temporarily) with a different device. Similarly, in the case of a medical emergency, it may not be possible to connect remotely to the pacemaker to access critical data. In such instances, valuable time and resources may be wasted.

Overall, even the most modern, conventional pacemakers cannot dynamically adjust their operation to best suit the patient's needs, given, for example, their activity level or surroundings. The resulting performance may be detrimental to the patient's health and lead to wasted resources.

In view of the foregoing, a need exists for methods and systems for controlling implantable medical devices that dynamically change the operation of the devices based on factors external to the body of the patient, such as his/her physiological state and/or surroundings.

To address these needs, the methods and systems of the present invention utilize, for example, data collected from one or more sensors on wearable devices to adjust the activity of implantable medical devices, such as pacemakers.

In some embodiments, methods for controlling an implantable cardiac device by one or more processors is provided. Data from at least one wearable device sensor is received. The implantable cardiac device is controlled based on the data.

The at least one wearable device sensor may be connected to a wearable device worn on a body of a user, and the implantable cardiac device may be implanted within the body of the user. The data may include, for example, at least one of a physiological condition of the user or a condition of the environment surrounding the user.

The at least one physiological condition of the user may include, for example, at least one of an activity level or body temperature. The condition of the environment surrounding the user may include, for example, at least one of an altitude, barometric pressure, or the presence of a magnetic field. The data further may further include genetic markers on the skin of the user.

In some embodiments, the implantable cardiac device is configured to pace a heart of the user, and the controlling of the implantable cardiac devices includes adjusting the rate at which the implantable cardiac device paces the heart.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 (and/or one or more processors described herein) is capable of being implemented and/or performing (or causing or enabling) any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, system memory 28 may include at least one program product having a set (e.g., at least one) of program modules that are configured to carry out the functions of embodiments of the invention.

Program/utility 40, having a set (at least one) of program modules 42, may be stored in system memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples include, but are not limited to: microcode, device drivers, redundant processing units, external disk drive arrays, RAID systems, tape drives, and data archival storage systems, etc.

In the context of the present invention, and as one of skill in the art will appreciate, various components depicted in FIG. 1 may be located in, for example, personal computer systems, hand-held or laptop devices, and network PCs. However, in some embodiments, some of the components depicted in FIG. 1 may be located in computing devices in, or associated with, wearable technology devices (or wearables or wearable devices), such as wristbands, wristwatches, earpieces, clothing, eyewear, headwear, etc., and/or implantable medical devices, such as implantable cardiac devices (e.g., pacemakers, defibrillators, and cardioverter-defibrillators (ICDs)). For example, some of the processing and data storage capabilities associated with mechanisms of the illustrated embodiments may take place locally via local processing components, while the same components are connected via a network to remotely located, distributed computing data processing and storage components to accomplish various purposes of the present invention. Again, as will be appreciated by one of ordinary skill in the art, the present illustration is intended to convey only a subset of what may be an entire connected network of distributed computing components that accomplish various inventive aspects collectively.

Figure 2:
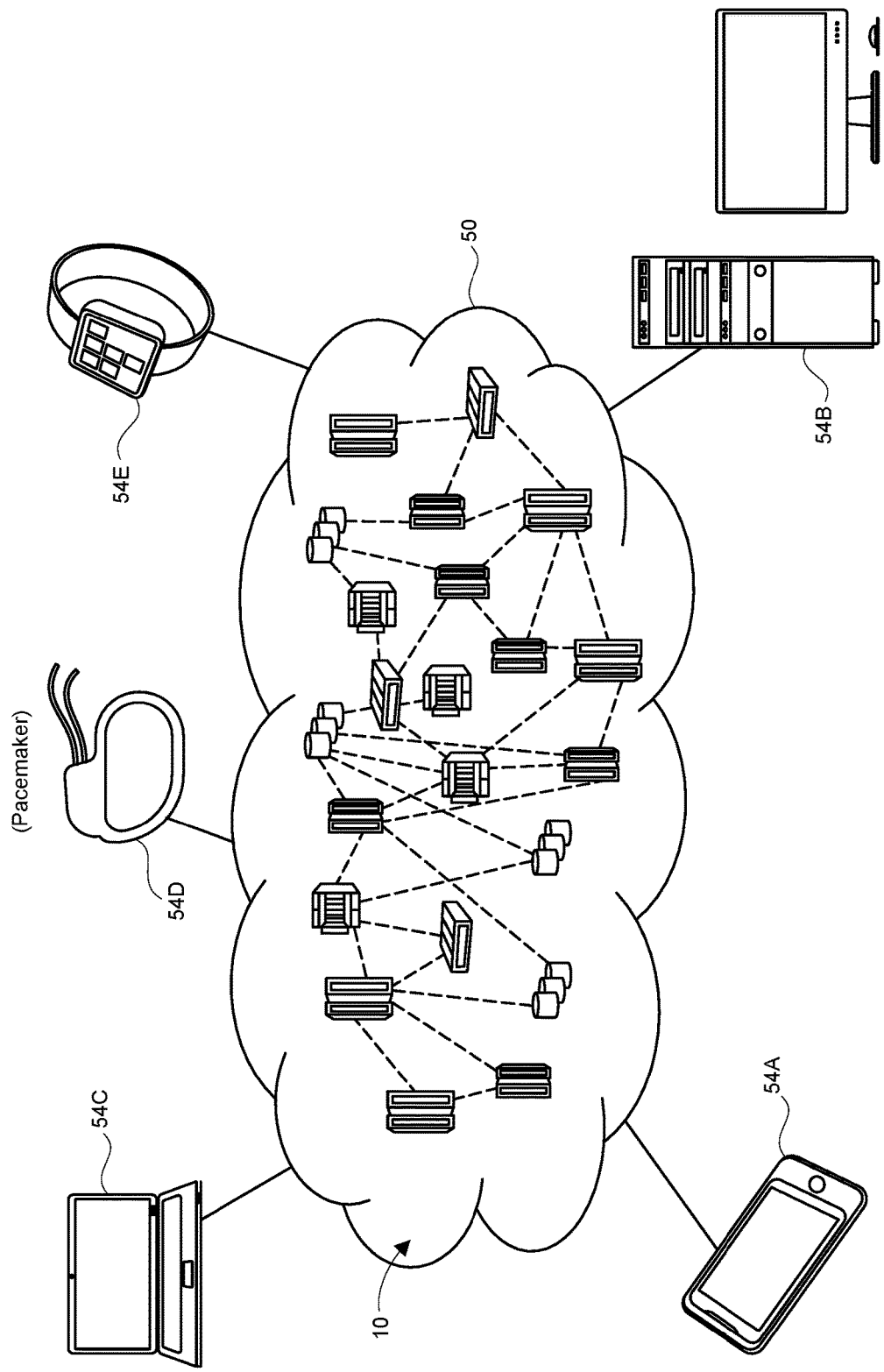
FIG. 2 is an additional block diagram depicting an exemplary cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, and/or laptop computer 54C, and others computer systems, such as, those in, or associated with, implantable medical devices (e.g., implantable cardiac devices) 54D and wearable devices 54E, may communicate.

Still referring to FIG. 2, nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-E shown in FIG. 2 are intended to be illustrative only and that computing nodes 10 and cloud computing environment 50 can communicate with any type of computerized device over any type of network and/or network addressable connection (e.g., using a web browser).

Figure 3:
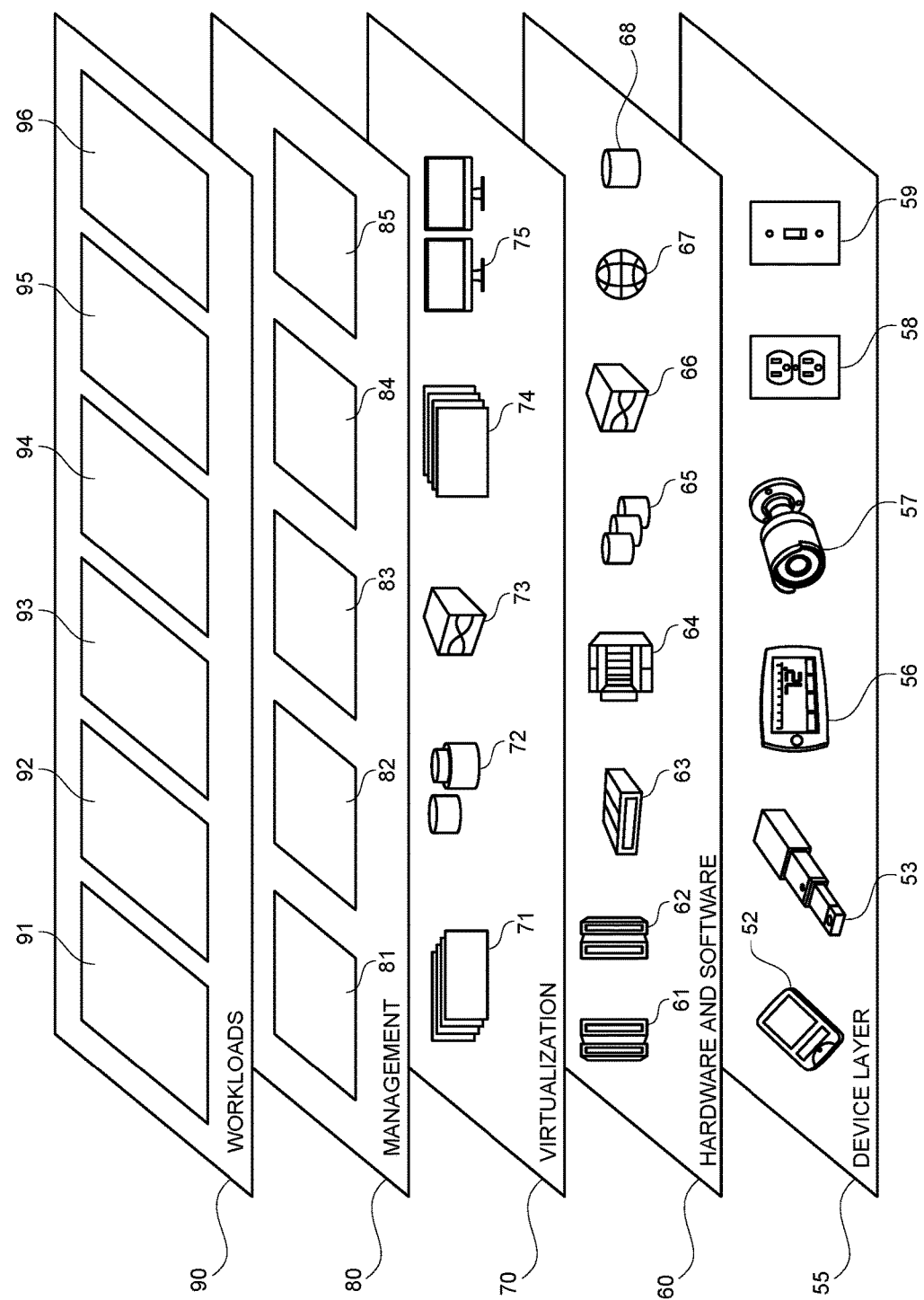
FIG. 3 is an additional block diagram depicting abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Device layer 55 includes physical and/or virtual devices, embedded with and/or standalone electronics, sensors, actuators, and other objects to perform various tasks in a cloud computing environment 50. Each of the devices in the device layer 55 incorporates networking capability to other functional abstraction layers such that information obtained from the devices may be provided thereto, and/or information from the other abstraction layers may be provided to the devices. In one embodiment, the various devices inclusive of the device layer 55 may incorporate a network of entities collectively known as the "internet of things" (IoT). Such a network of entities allows for intercommunication, collection, and dissemination of data to accomplish a great variety of purposes, as one of ordinary skill in the art will appreciate.

Device layer 55 as shown includes sensor 52, actuator 53, "learning" thermostat 56 with integrated processing, sensor, and networking electronics, camera 57, controllable household outlet/receptacle 58, and controllable electrical switch 59 as shown. Other possible devices may include, but are not limited to wearable technology devices (or wearables or wearable devices), such as wristbands, wristwatches, earpieces, clothing, eyewear, headwear, etc. and/or implantable medical devices, such as implantable cardiac devices (e.g., pacemakers, defibrillators, and ICDs), and various additional sensor devices, networking devices, electronics devices (such as a remote control device), additional actuator devices, so called "smart" appliances such as a refrigerator or washer/dryer, and a wide variety of other possible interconnected objects.

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provides cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and, in the context of the illustrated embodiments of the present invention, various workloads and functions 96 for collecting data from wearable devices and controlling implantable medical devices based on that data, as described herein. One of ordinary skill in the art will appreciate that the workloads and functions 96 may also work in conjunction with other portions of the various abstractions layers, such as those in hardware and software 60, virtualization 70, management 80, and other workloads 90 (such as data analytics processing 94, for example) to accomplish the various purposes of the illustrated embodiments of the present invention.

As previously mentioned, the methods and systems of the illustrated embodiments provide novel approaches for controlling an implantable medical device, such as an implantable cardiac device, by one or more processors. Data from at least one wearable device sensor is received. The implantable cardiac device is controlled based on the data. The at least one wearable device sensor may be connected to a wearable device worn on a body of a user, and the implantable cardiac device may be implanted within the body of the user. The data may include, for example, at least one of a physiological condition of the user or a condition of the environment surrounding the user. The at least one physiological condition of the user may include, for example, at least one of an activity level or body temperature. The condition of the environment surrounding the user may include, for example, at least one of an altitude, barometric pressure, or the presence of a magnetic field. The data further may further include genetic markers on the skin of the user. In some embodiments, the implantable cardiac device is configured to pace a heart of the user, and the controlling of the implantable cardiac devices includes adjusting the rate at which the implantable cardiac device paces the heart.

Figure 4:
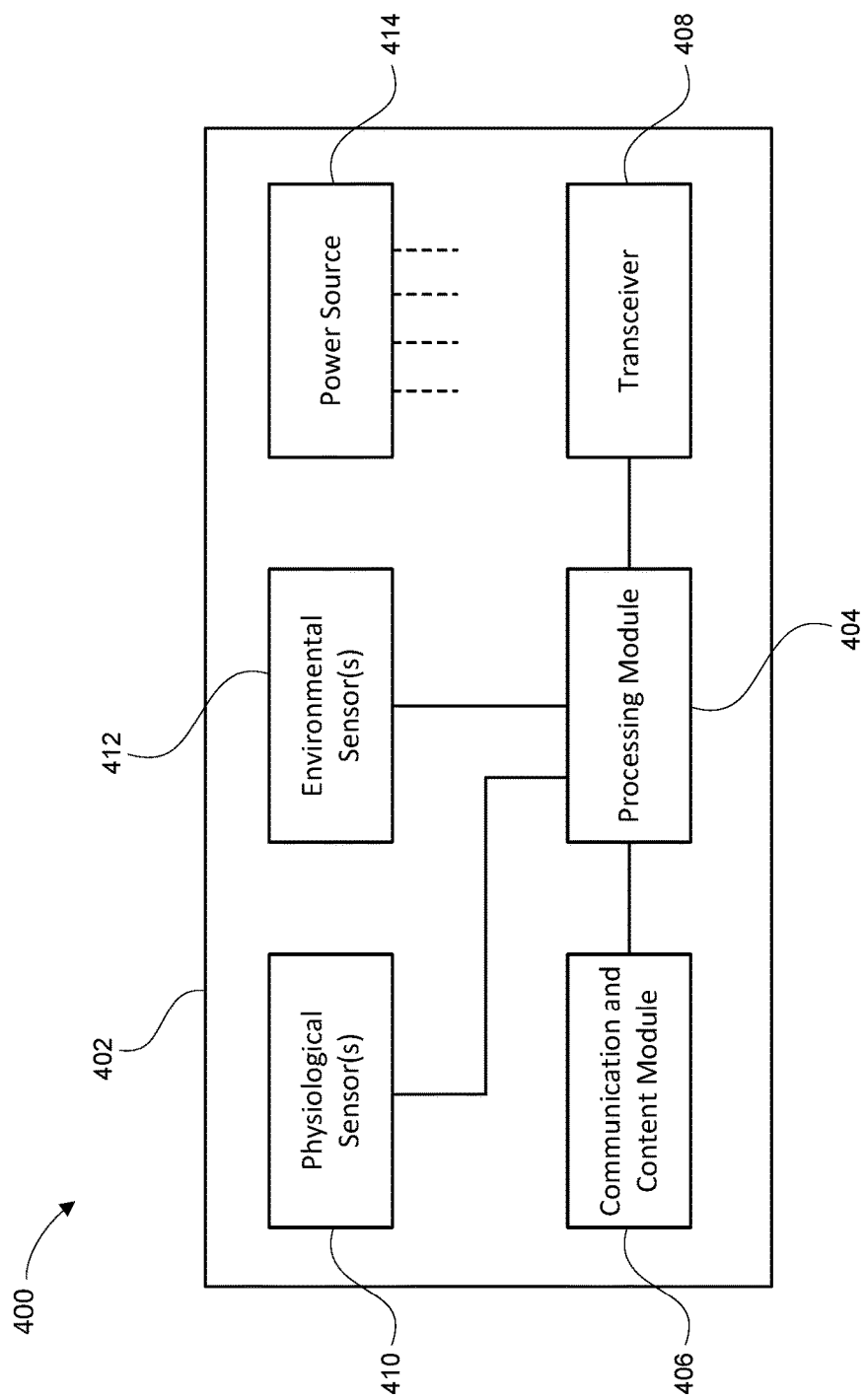
FIG. 4 is a block diagram depicting a wearable device according to an embodiment of the present invention.

FIG. 4 illustrates an exemplary wearable technology device (or wearable device or wearable) 400, according to some embodiments of the present invention. The wearable device 400 includes a housing (or body) 402. Although not shown in detail, the housing 402 may be in the form/shape of, for example, a wristband, wristwatch, earpiece, or any other wearable device and include one or more mechanisms (e.g., clips, bands, or straps), or be in a shape, suitable so that it may be worn on the body of a user (or patient). In some embodiments, the wearable device 400 is configured/intended primarily for human use. However, the wearable device may also be configured for use on animals, and the methods and systems described herein may be used on animals. Within (or coupled to) the housing 402, the wearable device 400 includes a processing module 404, a communication and content module 406, a transceiver 408, one or more physiological sensors 410, one or more environmental sensors 412, and a power source 414.

The communication and content module 406 may include, for example, a speaker, a microphone, and/or a display device and be configured to generate sounds and/or images received from the transceiver 408 and/or stored in a memory (e.g., within the processing module 404). For example, the communication and content module 406 may be used to play music, radio shows, videos, or other audio and/or visual entertainment and to communicate this information to a user of the wearable device 400. However, as described below, the communication and content module 406 may also be used to convey information concerning, for example, an implantable medical device to the user (and/or medical personnel) and/or make changes to the operation of the implantable medical device. It should be understood that the communication and content module 406 may not be included in some embodiments.

The transceiver 408 may include any receiver and/or transmitter, along with an antenna, suitable for, as an example, wireless communications using human-safe electromagnetic frequencies (e.g., LAN, radio waves, non-line-of-sight (NLOS) optical scatter, etc.).

The physiological sensor(s) 410 may include any type of sensor for monitoring the physiological functioning of the body of the user, such as, but not limited to, sensors for monitoring the following, as will be appreciated by one skilled in the art: heart rate, pulse rate, breathing rate, blood flow, heartbeat signatures, cardio-pulmonary health, organ health, metabolism, electrolyte type and concentration, physical activity, caloric intake, caloric metabolism, metabolomics, physical and psychological stress levels and stress level indicators, physiological and psychological response to therapy, drug dosage and activity (e.g., drug dosimetry), physiological drug reactions, drug chemistry in the body, biochemistry, position and balance, body strain, neurological functioning, brain activity, brain waves, blood pressure, cranial pressure, hydration level, auscultatory information, auscultatory signals associated with pregnancy, physiological response to infection, skin and core body temperature, eye muscle movement, blood volume, inhaled and exhaled breath volume, physical exertion, exhaled breath physical and chemical composition, the presence, identity, and concentration of viruses and bacteria, foreign matter in the body, internal toxins, heavy metals in the body, anxiety, fertility, ovulation, sex hormones, psychological mood, sleep patterns, hunger and thirst, hormone type and concentration, cholesterol, lipids, blood panel, bone density, body fat density, muscle density, organ and body weight, reflex response, sexual arousal, mental and physical alertness, sleepiness, auscultatory information, response to external stimuli, swallowing volume, swallowing rate, sickness, voice characteristics, tone, pitch, and volume of the voice, vital signs, head tilt, allergic reactions, inflammation response, auto-immune response, mutagenic response, DNA, proteins, protein levels in the blood, body hydration, water content of the blood, pheromones, internal body sounds, digestive system functioning, cellular regeneration response, healing response, stem cell regeneration response, etc. As non-limiting examples, the physiological sensor(s) 410 may include an impedance plethysmograph to monitor blood pressure and/or changes in volume within an organ or the body of a user, a microphone to detect various sounds made by the patient, such as coughing, sneezing, laughing, crying, etc., electrodes to detect changes in pH levels (via changes in open-circuit potential), an electrocardiogram (ECG), and motion sensors.

The environmental sensor(s) 412 may include any suitable sensors for monitoring the external environment in the vicinity of/surrounding the body of the user, such as, but not limited to the following, as will be appreciated by one skilled in the art: climate/weather conditions, humidity, temperature, pressure, barometric pressure, pollution, automobile exhaust, soot density, airborne particle density, airborne particle size, airborne particle shape, airborne particle identity, volatile organic chemicals (VOCs), hydrocarbons, polycyclic aromatic hydrocarbons (PAHs), carcinogens, toxins, electromagnetic energy (e.g., optical radiation, X-rays, gamma rays, microwave radiation, terahertz radiation, ultraviolet radiation, infrared radiation, radio waves, and the like), magnetic fields/EMF energy, atomic energy (e.g., alpha particles, beta-particles, gamma rays, and the like), gravity, light properties (e.g., intensity, frequency, flicker, and phase), ozone, carbon monoxide, greenhouse gases, carbon dioxide, nitrous oxide, sulfides, airborne pollution, foreign material in the air, biological particles (e.g., viruses, bacteria, and toxins), signatures from chemical weapons, wind, air turbulence, sound and acoustical energy (both human audible and inaudible), ultrasonic energy, noise pollution, human voices, animal sounds, diseases expelled from others, the exhaled breath and breath constituents of others, toxins from others, bacteria and viruses from others, pheromones from others, industrial and transportation sounds, allergens, animal hair, pollen, exhaust from engines, vapors and fumes, fuel, signatures for mineral deposits or oil deposits, snow, rain, thermal energy, hot surfaces, hot gases, solar energy, hail, ice, vibrations, traffic, the number of people in a vicinity of the user, the number of people encountered throughout the day, coughing and sneezing sounds from people in the vicinity of the user, loudness and pitch from those speaking in the vicinity of the user, etc. In one particular example, the environmental sensor(s) includes a microelectromechanical systems (MEMS) device configured to detect presence and strength of magnetic fields. The environmental sensor(s) 412 may be also configured to determine the location of the user, via, for example, the Global Positioning System (GPS), wireless signals (e.g., through triangulation), cellular infrastructure, etc., as is commonly understood.

In some embodiments, one or more of the physiological sensor(s) 410 and/or the environmental sensor(s) 412 is configured to identify the particular user wearing the wearable device 400, via biometric identification data, such as genetic markers (e.g., on the skin of the user).

The power source 414 is suitably coupled to the other components within the wearable device 400 and may include any device suitably configured to power the other components of the wearable device 400. In some embodiments, the power source 414 is a portable rechargeable lithium-polymer or zinc-air battery. The power source 414 may (also) include one or more energy-harvesting mechanisms, such as piezoelectric devices, MEMS devices, thermoelectric devices, thermovoltaic devices, etc., configured to collect and store energy from body movements, electromagnetic energy, thermal energy, temperature gradients, etc.

Figure 5:
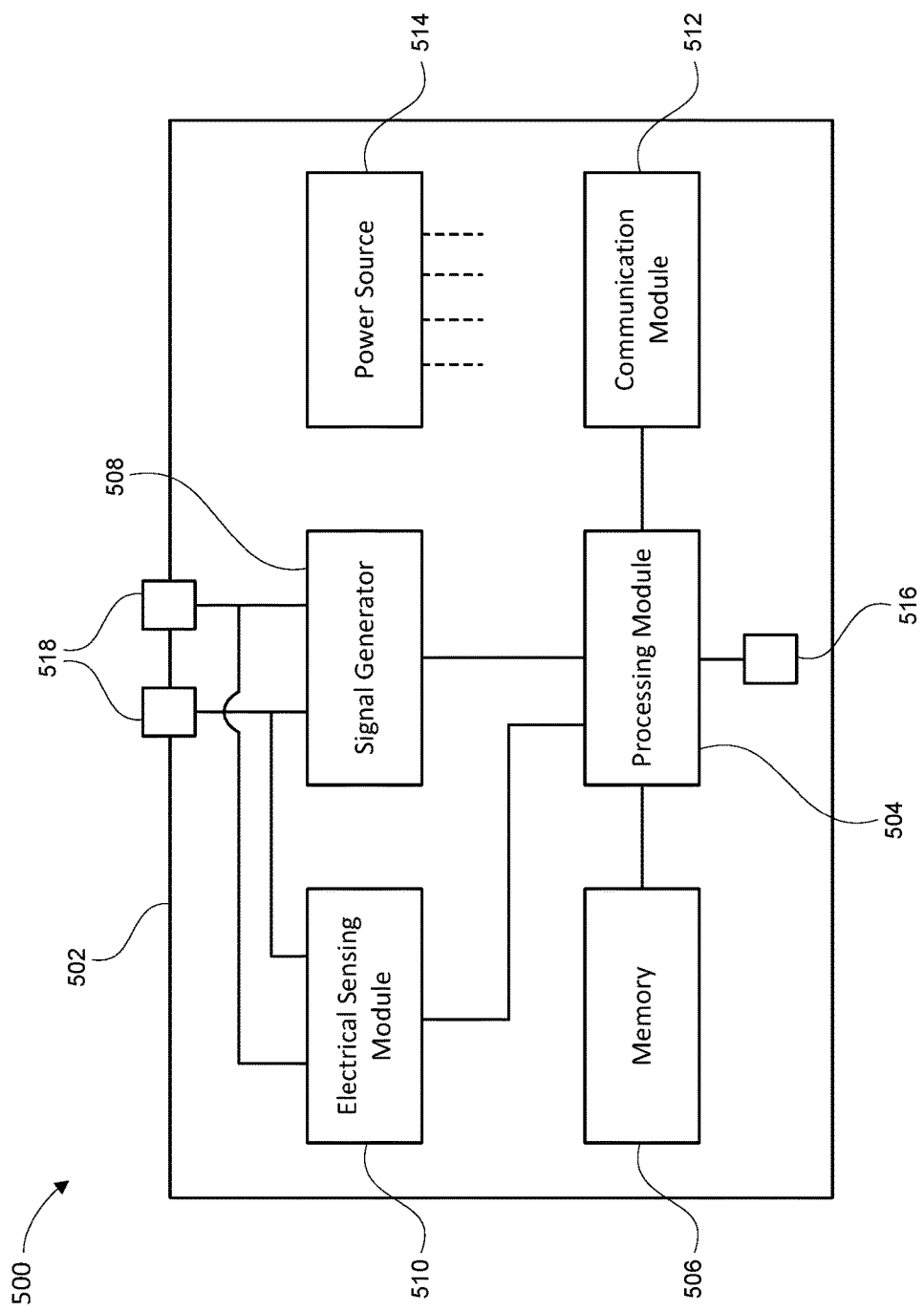
FIG. 5 is a block diagram depicting an implantable medical device according to an embodiment of the present invention.

FIG. 5 illustrates an implantable medical device, in particular an implantable cardiac device (or cardiac device), 500, according to some embodiments of the present invention. In some embodiments, the implantable cardiac device 500 is a pacemaker or an ICD with pacemaker functionality (e.g., atrial and/or ventricular). The cardiac device 500 includes a housing (or body) 502 with a processing module 504, a memory 506, a signal generator (or signal generator module) 508, an electrical sensing module 510, a communication module 512, a power source 514, a sensor 516, and electrodes 518. The various components shown in FIG. 5 represent functionality that may be incorporated into the implantable medical (e.g., cardiac) devices described herein. The components may include any discrete and/or integrated electronic circuit components that implement analog and/or digital circuits capable of producing the functionality described herein.

The processing module 504 may be (or include) one or more processors or computing devices as described above. The processing module 504 is in operable communication with the other components of the cardiac device 500 and may be configured to control the operation of the cardiac device 500 in accordance with the methods and systems described herein.

The memory 506 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device on which instructions are stored, which executed (e.g., by the processing module and/or one or more processors described herein) cause the components to perform various functions described herein. For example, the memory 506 may include pacing (atrial and/or ventricular) instructions and values, such as a baseline pacing rate, a baseline pacing interval and the baseline AV interval, as is commonly understood.

The electrical sensing module 510 may include circuits that acquire electrical signals, such as intrinsic atrial and/or intrinsic ventricular cardiac electrical activity, and otherwise monitor electrical activity of the heart through electrodes 518. The electrical sensing module 510 may filter, amplify, and digitize the acquired electrical signals to generate raw digital data. The processing module 504 may receive the digitized data generated by electrical sensing module 510. In some examples, processing module 504 may perform various digital signal processing operations on the raw data, such as digital filtering. The signal generator module 508 is configured to deliver electrical stimulation (e.g., pacing pulses) to the heart (e.g., to an atrium and/or ventricle) via the electrodes 518 based on commands from the processing module 504.

Processing module 504 may sense cardiac events based on the data received from electrical sensing module 510. For example, the processing module 504 may sense cardiac events based on the data received from electrical sensing module 510. In some examples, the processing module 504 may sense ventricular activation based on the data received from the electrical sensing module 510. For example, the processing module 504 may detect far-field R-waves (FFRWs) indicative of ventricular activation based on the data received from the electrical sensing module 510.

The communication module 512 may include any suitable hardware (e.g., an antenna), firmware, software, or any combination thereof for communicating with another device, such the wearable device 400 shown in FIG. 4 and described above. For example, the communication module 512 may include a transceiver (or receiver or transmitter) suitable for, as an example, wireless communications using human-sage electromagnetic frequencies (e.g., LAN, radio waves, non-line-of-sight (NLOS) optical scatter, etc.).

The power source 514 is suitably coupled to the other components within the cardiac device 500 and may include, for example, a rechargeable or non-rechargeable battery, such as a lithium battery. The sensor(s) 516 may include, for example, an accelerometer and/or a pressure sensor. An accelerometer may generate signals that indicate the acceleration of the cardiac device 500. A pressure sensor may generate signals that indicate pressure within a chamber of the heart (e.g., atrium and/or ventricle).

Figure 6:
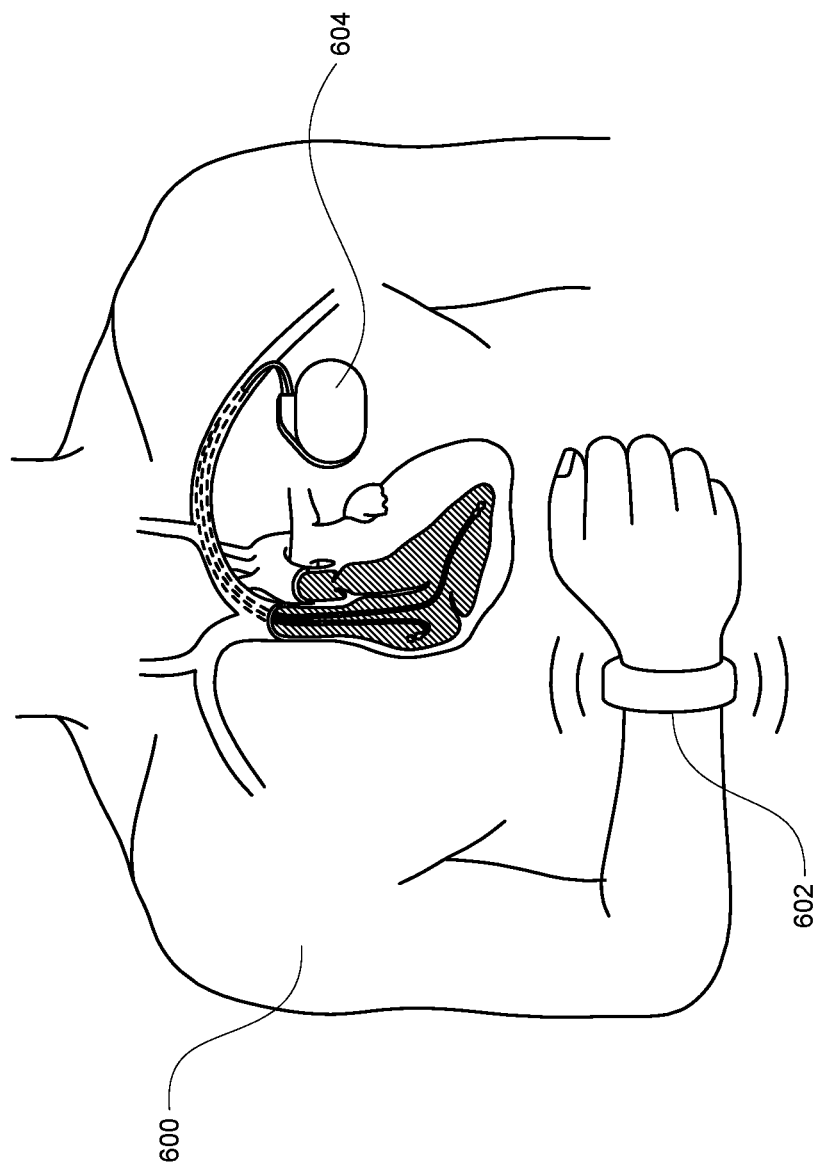
FIG. 6 is a simplified view of a body of a user having an implantable medical device deployed within and a wearable device worn thereon.
Figure 7:
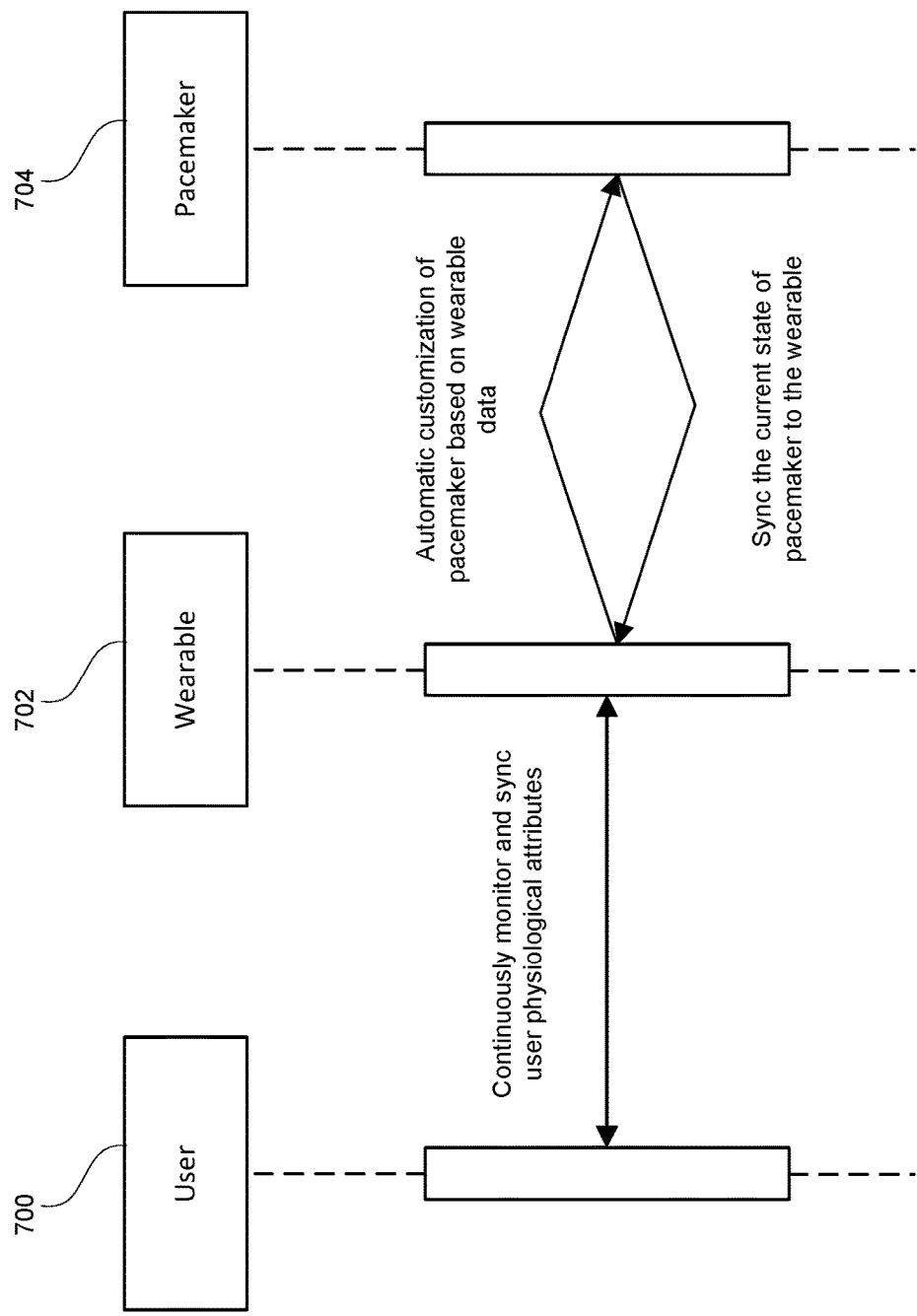
FIG. 7 is a simplified block diagram schematic/interface view of a user, a wearable device, and a pacemaker according to an embodiment of the present invention.

FIG. 6 illustrates a body 600 of a user (or patient). As is shown, a wearable device (or wearable) 602 is being worn, and a cardiac device (e.g., a pacemaker) 604 is implanted within, the body 600. The wearable 602 and the pacemaker 604 may be similar to the wearable device 400 and cardiac device 500 shown in FIGS. 4 and 5, respectively, and described. FIG. 7 illustrates the user (i.e., the body thereof) 600 of the patient, the wearable 602, and the pacemaker 604 in a simplified block diagram schematic/interface manner. In at least some embodiments, the wearable 602 (i.e., one or more sensors thereon) collects information/data about the user 600 and/or the surroundings (or environment) of the user 600. The data is provided to the pacemaker 604 (e.g., via wireless communication), and the pacemaker 604 adjusts its operation (e.g., pacing type, rate, etc.) based on the data when/if appropriate. For example, as shown in FIG. 7, in some embodiments, the wearable 602 continuously monitors physiological (and environmental) attributes associated with the user 600 and syncs its data to those attributes, and that data is sent to the pacemaker 604 where it is used to automatically customize the operation/functionality of the pacemaker 604. In some embodiments, information related to the current state/operation of the pacemaker 604 is sent back to the wearable 602 where it may be retrieved and/or viewed by the user 600 and/or medical personnel.

In some embodiments, before data from the wearable 602 is used to control and/or adjust the operation of the pacemaker 604, the wearable 602 registers/is associated with the pacemaker 604. For example, the wearable 602 may provide the pacemaker 604 with biometric identification data specific to the user 600, such as genetic markers on the skin of the user 600, which is stored in the pacemaker 604. After such a registration process is completed, the biometric data (e.g., genetic markers) is included with any other data sent by the wearable 602 so that the pacemaker 604 can ensure that the other data being received is associated with the same user 600 (i.e., to make sure the data is not associated with another person). As described above, the other data sent by the wearable 602 may include physiological conditions of the user 600, such as the user's activity level (e.g., sleeping, idle, exercising, etc.), as well as the times at which such conditions were observed. Other physiological parameters may also be included, such as body temperature, pH level, or any other type of data the wearable 602 is configured to collect (as described herein). The wearable 602 may also scan the surroundings of the user 600 for environmental conditions that may affect the operation of the pacemaker and/or the physiological state of the user 600, such as the presence of magnetic fields, altitude, barometric pressure, longitude/latitude, etc. This data is used by the pacemaker 604 to adjust, for example, the type and/or rate of pacing performed if/when appropriate.

For example, if the data from the wearable 602 indicates that the user 600 is at a particular level of activity, such as sleeping or exercising, the pacemaker 604 may adjust the type and/or rate of pacing to match (and/or be appropriate for) that activity level. The data from the wearable 602 may also indicate a particular health profile of the user 600 based on various parameters such as basal metabolic rate (BMR), body mass index (BMI), metabolic age, muscle mass, body fat percentage, weight, visceral fat, subcutaneous fat, etc., which may also be used by the pacemaker 604 to adjust the pacing. Additionally, environmental conditions, such as the presence of a magnetic field, may also be detected by the wearable 602 and included in the data sent to the pacemaker 604. If appropriate, the pacemaker 604 may adjust the pacing (also) based on such environmental conditions and/or the wearable 602 may generate an indication of the environmental condition (e.g., the wearable 602 may generate an aural message to alert the user 600 of the presence of a magnetic field).

As such, embodiments described herein provide methods and systems in which data collected from wearable devices may be used to dynamically control and/or adjust the operation of implantable medical devices, such as pacemakers and other implantable cardiac devices. As a result, the efficiency with which patient health is managed may be improved and resources (e.g., battery life) may be conserved.

Additionally, in some embodiments, the wearable 602 may be used to service and monitor the pacemaker 604. For example, for wearable 602 may receive (e.g., via wireless communication) a software upgrade for the pacemaker 604 and send/upload the new software to the pacemaker 604 when appropriate/required. Further, in some embodiments, the wearable 602 may be used to monitor the previous (and/or current) operation of the pacemaker 604. For example, the wearable 602 may receive various data from the pacemaker 604, such as the type and/or rate of pacing at certain times or other cardiac events, perhaps along with actions taken by the pacemaker 604 during such events. In such embodiments, the wearable 602 may provide a "dashboard" (e.g., on a display device thereon) for the user (and/or medical personnel) to view this data and/or any other suitable information related to the pacemaker 604. Similarly, the wearable 602 may provide an interface with which manual adjustments to the pacemaker's 604 operation may be made (e.g., by medical personnel).

Figure 8:
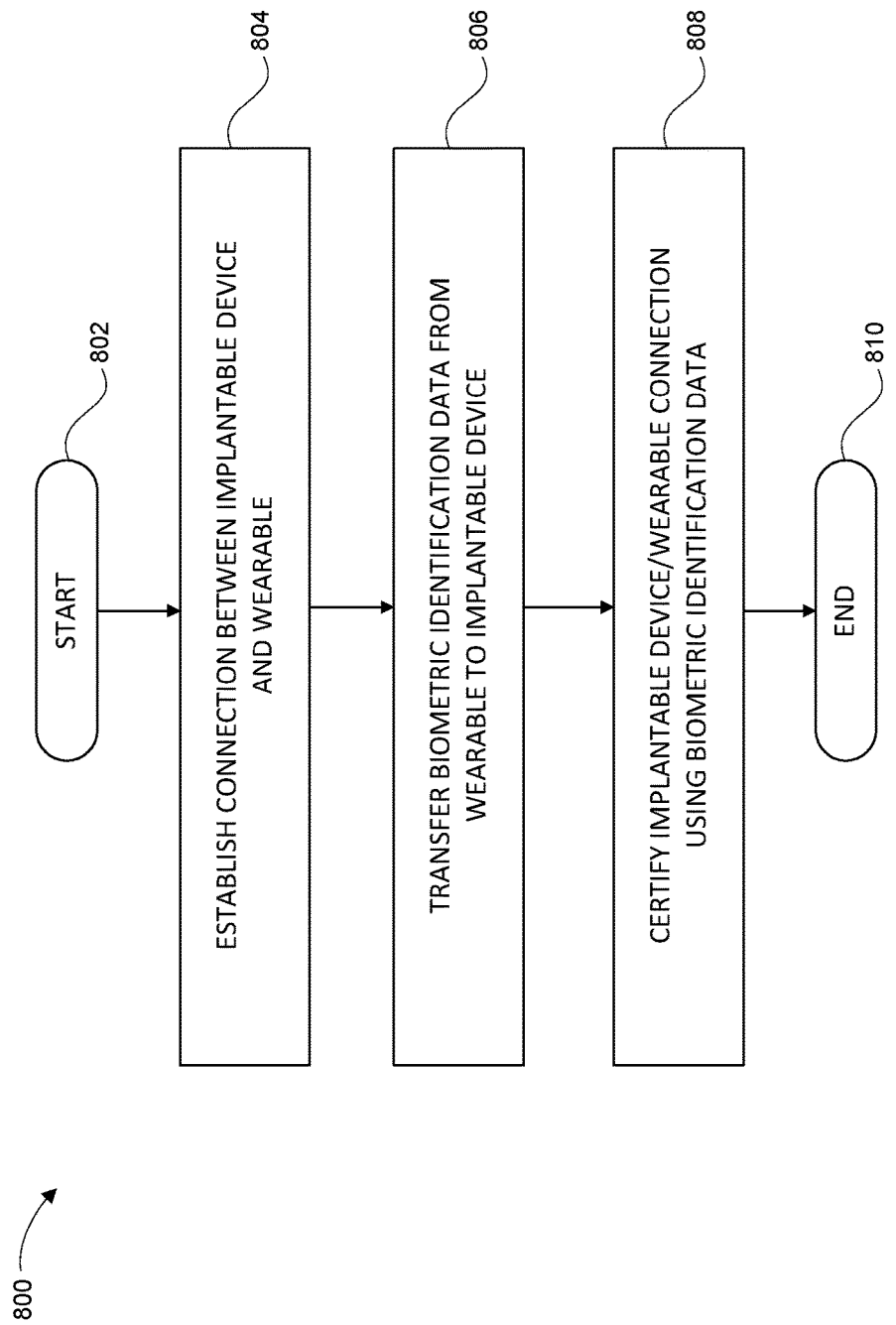
FIG. 8 is a flowchart diagram depicting an exemplary method in which various aspects of the present invention may be implemented.

Turning to FIG. 8, a flowchart diagram of an exemplary method 800 in which various aspects of the embodiments described herein may be implemented. Method 800 begins (step 802) with, for example, an implantable device (i.e., an implantable medical device) being implanted (or deployed or installed) within a body of a user (or patient) and a wearable (i.e., a wearable device) being put (or worn) on the body of the user. The implantable device may be an implantable cardiac device with pacemaker functionality, and the wearable may be, for example, in the form of a wristband, watch, earpiece, etc., such as those described above.

A connection between the implantable device and the wearable is established (step 804). As described above, the connection may be in the form of wireless communications enabled by any suitable transmitters and/or receivers within the implantable device and the wearable.

Biometric identification data is transferred from the wearable to the implantable device (step 806). As described above, the biometric identification data may include genetic markers on the skin of the user, which are detected by the wearable.

The connection between the implantable device and the wearable device is then certified using the biometric identification data (step 808). The certification may be performed by an appropriate medical authority (e.g., a doctor or other medical personnel) and may serve as a way for the wearable device and/or the user to be "registered" with the implantable device. As described above, in some embodiments, the biometric identification data is (re)sent from the wearable device to the implantable device along with other data (e.g., physiological and/or environmental data) collected by the wearable to ensure that the data being received by the implantable device is associated with the user (i.e., the body of the user in which the implantable device is deployed).

Method 800 ends (step 810) with, for example, the operation of the implantable device being controlled and/or adjusted based on data collected by the wearable and transmitted to the implantable device, as described herein. It should be understood that method 800 may include any additional steps in accordance with the various embodiments described herein.

Figure 9:
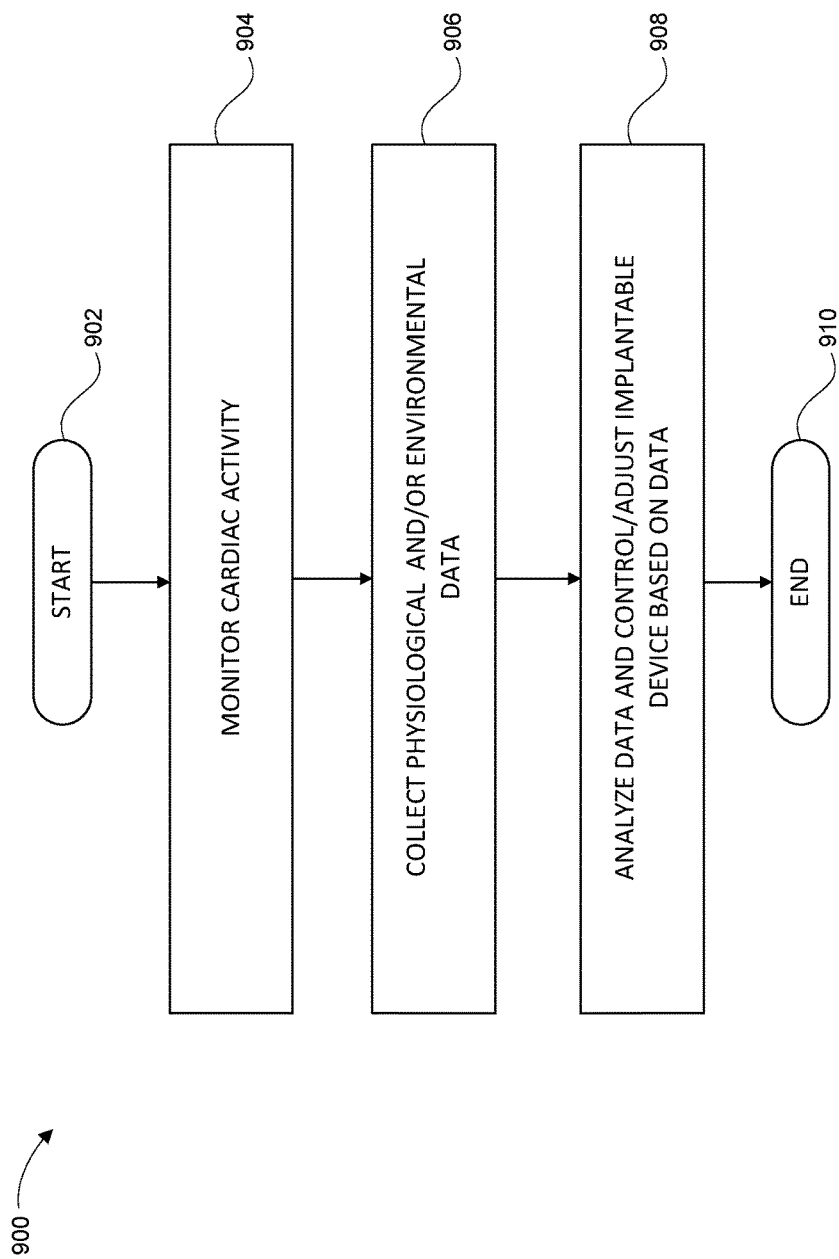
FIG. 9 is a flowchart diagram depicting an exemplary method, again in which various aspects of the present invention may be implemented.

Turning to FIG. 9, a flowchart diagram of an exemplary method 900 in which various aspects of the embodiments described herein may be implemented. Method 900 begins (step 902) with, for example, an implantable device (i.e., an implantable medical device) being implanted (or deployed or installed) within a body of a user (or patient) and a wearable (i.e., a wearable device) being put (or worn) on the body of the user. The implantable device may be an implantable cardiac device with pacemaker functionality, and the wearable may be, for example, in the form of a wristband, watch, earpiece, etc., such as those described above.

Cardiac activity is monitored (step 904) with, for example, the implantable device and/or the wearable. The monitoring of cardiac activity may include detecting the heartbeat of the user's heart and/or detecting any sort of undesirable cardiac events, such as arrhythmias. Although not specifically shown in FIG. 9, in some embodiments, the implantable device may take appropriate action if any undesirable cardiac events are detected (e.g., changing pacing type and/or rate, defibrillation, etc.)

Physiological and/or environment data is collected by, for example, the wearable (step 906). As described above, the data may be collected using one or more sensors on, or within, the wearable, and may include various types of physiological data (e.g., breathing rate, pH levels, body temperature, etc.) and/or environmental data (e.g., the presence of a magnetic field, altitude, etc.), as described above.

The physiological and/or environmental data is analyzed, and if appropriate, the operation of the implantable device is controlled and/or adjusted based on the data (step 908). In some embodiments, the data is analyzed by/within the wearable, but it may (also) be analyzed by/within the implantable device. For example, in some embodiments, the data is analyzed by the wearable, which sends instructions/commands to the implantable device to control/adjust the operation thereof (e.g., pacing type and/or rate), if appropriate. However, in some embodiments, the data is sent to the implantable device by the wearable, where it is analyzed and the determination is made whether or not to control/adjust the operation of the implantable device.

Method 900 ends (step 910) with, for example, the operation of the implantable device continuing in the appropriate manner. Although not shown in FIG. 9, it should be understood that method 900 may be continuously repeated so that the operation of the implantable device may be continuously/dynamically updated based on the most current physiological and/or environmental data collected by the wearable. It should also be understood that method 900 may include any additional steps in accordance with the various embodiments described herein.

Figure 10:
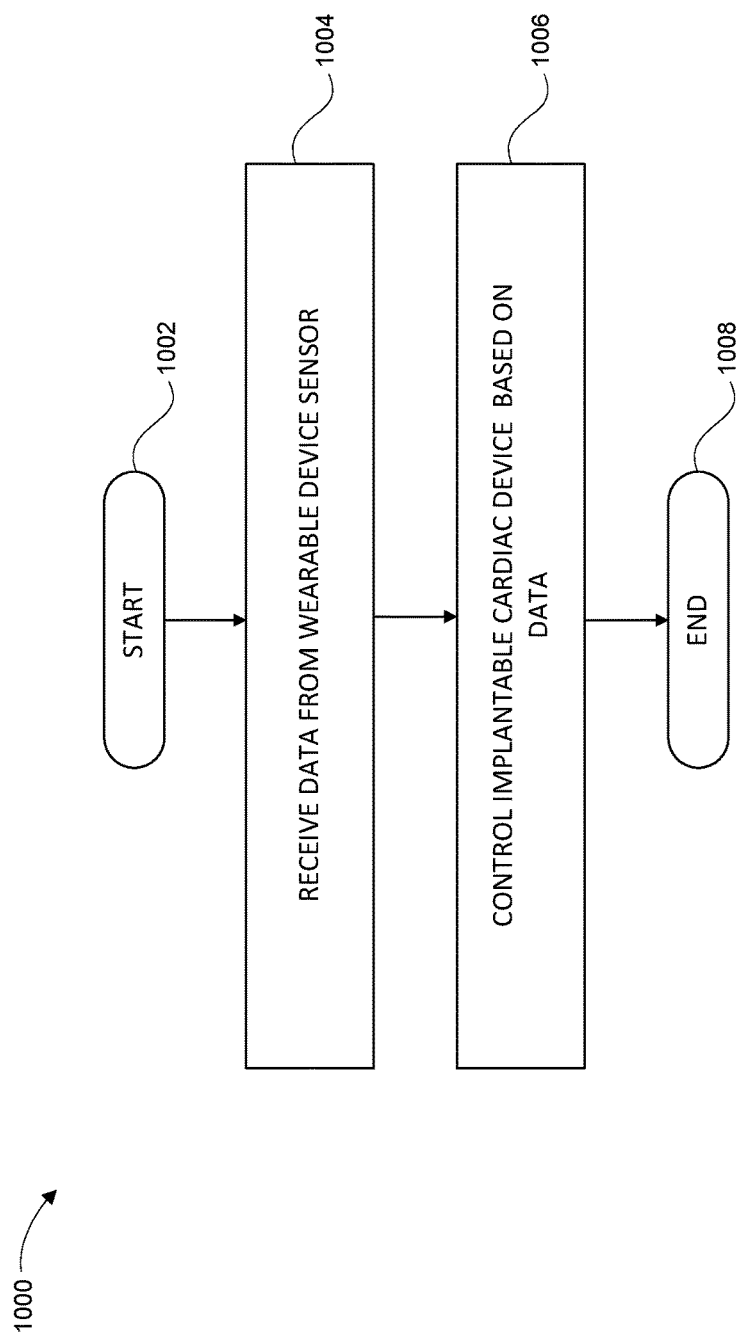
FIG. 10 is a flowchart diagram depicting an exemplary method, again in which various aspects of the present invention may be implemented.

Turning to FIG. 10, a flowchart diagram of a simplified method 1000 in which various aspects of the embodiments described herein may be implemented. Method 1000 begins (step 1002) with, for example, an implantable cardiac device being implanted (or deployed or installed) within a body of a user (or patient) and a wearable (i.e., a wearable device) being put (or worn) on the body of the user. The implantable cardiac device may have pacemaker functionality, and the wearable may be, for example, in the form of a wristband, watch, earpiece, etc., such as those described above.

Data, such as physiological and/or environmental data, is received from one or more wearable device sensors (step 1004). As described above, the data may be collected using one or more sensors on, or within, the wearable, and may include various types of physiological data (e.g., breathing rate, pH levels, body temperature, etc.) and/or environmental data (e.g., the presence of a magnetic field, altitude, etc.).

The implantable cardiac device is controlled (and/or the operation thereof is adjusted) based on the data from the wearable device sensor(s) (step 1008). In embodiments in which the implantable cardiac device has pacemaker functionality, the controlling/adjusting of the operation may include changing the type and/or rate of pacing performed by the device.

Method 1000 ends (step 1010) with, for example, the operation of the implantable cardiac device continuing in the appropriate manner. Although not shown in FIG. 10, it should be understood that method 1000 may be continuously repeated so that the operation of the implantable cardiac device may be continuously/dynamically updated based on the most current physiological and/or environmental data collected by the wearable. It should also be understood that method 1000 may include any additional steps in accordance with the various embodiments described herein.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowcharts and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowcharts and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowcharts and/or block diagram block or blocks.

The flowcharts and block diagrams in the Figures illustrate the architecture, functionality, and operation of possible implementations of systems, methods, and computer program products according to various embodiments of the present invention. In this regard, each block in the flowcharts or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts or carry out combinations of special purpose hardware and computer instructions.

The invention claimed is:

1. A method, by a one or more processors, for controlling an implantable cardiac device, comprising:
   registering a wearable device including at least one wearable device sensor with the implantable cardiac device at a first time; wherein the registering includes transmitting biometric identification data specific to a user from the wearable device to the implantable cardiac device;
   receiving data from the at least one wearable device sensor at a second time, the data including the biometric identification data registered to the user, a physiological condition of the user, and a condition of the environment surrounding the user;
   controlling the implantable cardiac device based on the data; and
   generating an indication on the wearable device of the physiological condition of the user and the condition of the environment surrounding the user commensurate with controlling the implantable cardiac device.

2. The method of claim 1, wherein the at least one wearable device sensor is connected to the wearable device worn on a body of the user, and the implantable cardiac device is implanted within the body of the user.

3. The method of claim 1, wherein the data includes a physiological condition of the user, wherein the physiological condition of the user includes at least one of an activity level or body temperature.

4. The method of claim 1, wherein the data includes a condition of the environment surrounding the user, wherein the condition of the environment surrounding the user includes at least one of an altitude, barometric pressure, or the presence of a magnetic field.

5. The method of claim 1, wherein the implantable cardiac device is configured to pace a heart of the user, and wherein the controlling of the implantable cardiac device includes adjusting the rate at which the implantable cardiac device paces the heart.

6. The method of claim 1, wherein the data further includes genetic markers on the skin of the user.

7. A system for controlling an implantable cardiac device, comprising:
   a wearable device;
   at least one sensor connected to the wearable device; and
   at least one processor in communication with the at least one sensor and the wearable device, that
      registers the wearable device including the at least one wearable device sensor with the implantable cardiac device at a first time; wherein the registering includes transmitting biometric identification data specific to a user from the wearable device to the implantable cardiac device;
      receives data from the at least one wearable device sensor at a second time, the data including the biometric identification data registered to the user, a physiological condition of the user, and a condition of the environment surrounding the user;
      controls the implantable cardiac device based on the data; and
      generates an indication on the wearable device of the physiological condition of the user and the condition of the environment surrounding the user commensurate with controlling the implantable cardiac device.

8. The system of claim 7, wherein the wearable device is worn on a body of the user, and the implantable cardiac device is implanted within the body of the user.

9. The system of claim 7, wherein the data includes a physiological condition of the user, wherein the physiological condition of the user includes at least one of an activity level or body temperature.

10. The system of claim 7, wherein the data includes a condition of the environment surrounding the user, wherein the condition of the environment surrounding the user includes at least one of an altitude, barometric pressure, or the presence of a magnetic field.

11. The system of claim 7, wherein the implantable cardiac device is configured to pace a heart of the user, and wherein the controlling of the implantable cardiac device includes adjusting the rate at which the implantable cardiac device paces the heart.

12. The system of claim 7, wherein the data further includes genetic markers on the skin of the user.

13. A computer program product for controlling an implantable cardiac device by one or more processors, the computer program product comprising a non-transitory computer-readable storage medium having computer-readable program code portions stored therein, the computer-readable program code portions comprising:
    an executable portion that registers a wearable device including at least one wearable device sensor with the implantable cardiac device at a first time; wherein the registering includes transmitting biometric identification data specific to a user from the wearable device to the implantable cardiac device;
    an executable portion that receives data from the at least one wearable device sensor at a second time, the data including the biometric identification data registered to the user, a physiological condition of the user, and a condition of the environment surrounding the user;
    an executable portion that controls the implantable cardiac device based on the data; and
    an executable portion that generates an indication on the wearable device of the physiological condition of the user and the condition of the environment surrounding the user commensurate with controlling the implantable cardiac device.

14. The computer program product of claim 13, wherein the at least one wearable device sensor is connected to the wearable device worn on a body of the user, and the implantable cardiac device is implanted within the body of the user.

15. The computer program product of claim 13, wherein the data includes a physiological condition of the user, wherein the physiological condition of the user includes at least one of an activity level or body temperature.

16. The computer program product of claim 13, wherein the data includes a condition of the environment surrounding the user, wherein the condition of the environment surrounding the user includes at least one of an altitude, barometric pressure, or the presence of a magnetic field.

17. The computer program product of claim 13, wherein the implantable cardiac device is configured to pace a heart of the user, and wherein the controlling of the implantable cardiac device includes adjusting the rate at which the implantable cardiac device paces the heart.

18. The computer program product of claim 13, wherein the data further includes genetic markers on the skin of the user.

\* \* \* \* \*